United States Patent [19]

Dolfini et al.

[11] 4,026,886

[45] May 31, 1977

[54] 7-ACYL-7-ARYLTHIOCEPHALOSPORINS

[75] Inventors: Joseph Edward Dolfini; Ekkehard Bohme, both of Cincinnati, Ohio

[73] Assignee: E. R. Squibb & Sons, Inc., Princeton, N.J.

[22] Filed: Jan. 23, 1976

[21] Appl. No.: 651,742

Related U.S. Application Data

[60] Division of Ser. No. 480,789, June 19, 1974, Pat. No. 3,954,744, which is a division of Ser. No. 260,620, June 7, 1972, Pat. No. 3,840,533, which is a continuation-in-part of Ser. No. 174,510, Aug. 24, 1971, abandoned.

[52] U.S. Cl. .............................. 260/243 C; 424/246
[51] Int. Cl.² ....................................... C07D 501/20
[58] Field of Search ................................ 260/243 C

[56] References Cited

UNITED STATES PATENTS 3,954,744  5/1976  Dolfini .......................... 260/243 C

*Primary Examiner*—Nicholas S. Rizzo
*Attorney, Agent, or Firm*—Lawrence S. Levinson; Merle J. Smith; Stephen B. Davis

[57] ABSTRACT

Disclosed herein are cephalosporanic acid and novel derivatives thereof which are substituted in the 7-position, processes for preparing such compounds and the utility thereof. The compounds of the invention have been found to be useful as antibacterial agents.

9 Claims, No Drawings

7-ACYL-7-ARYLTHIOCEPHALOSPORINS

This application is a division of Ser. No. 480,789 filed on June 19, 1974, now U.S. Pat. No. 3,954,744, which was a division of Ser. No. 260,620 filed on June 7, 1972, now U.S. Pat. No. 3,840,533, which was a continuation-in-part of application Ser. No. 174,510 filed on Aug. 24, 1971, now abandoned.

SUMMARY OF THE INVENTION

This invention relates to 7-substituted-7-amino-cephalosporanic acid having the following Formula I:

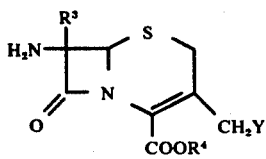

wherein $R^3$ is alkylsulfonyl, arylsulfonyl, aralkylsulfonyl, cyano, halogen, aralkoxy, acyl, arylthio, alkylthio, and alkyl having electronegative substituents therein such as halogen, cyano, perfluoro lower alkyl, substituted carbalkoxy, dialkylaminoalkyl, alkoxy, acyloxy, and $R^4$ is hyrogen, lower alkyl, aralkyl, substituted alkyl, substituted aralkyl or cation; Y is hydrogen, acetoxy, pyridinium, alkoxy, alkyl, mercapto, hydroxy or alkylamino. These compounds have been found to be useful as antibacterial agents and as intermediates in the preparation of 7-acylamino-7-substituted cephalosporanic acids and pharmaceutically acceptable salts thereof.

DESCRIPTION OF INVENTION

This invention relates to novel 7-substituted-7-aminocephalosporanic acid and derivatives thereof which are active as antibacterial agents and are valuable intermediates utilized in the preparation of the acylated derivatives. The 7-substituted-7-aminocephalosporanic acids and salts of this invention also possess antibacterial activity which is enhanced by acylation of the 7-amino group. In Formulae I and V the term pharmaceutically acceptable cation means an alkali metal (e.g., sodium and potassium), an alkaline earth metal (e.g., calcium and magnesium), ammonium, or an amine, such as a lower alkyl amine (e.g., methylamine), a di(lower alkyl)amine (e.g., diethylamine), a phenyl-lower alkylamine (e.g., benzylamine), a di(phenyl-lower alkyl)amine (e.g., dibenzylamine), or an alkylenediamine (e.g., N,N'-dibenzylethylenediamine), or the like. In the case where Y = pyridinium or quarternary ammonium, $R^4$ is represented by an anion.

Compounds of Formula I are prepared by reacting a Schiff's base of 7-aminocephalosporanic acid of Formula II:

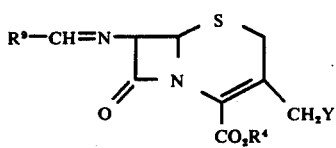

wherein $R^9$ is phenyl, X-substituted phenyl, lower alkyl or aralkyl (e.g., benzyl or phenethyl), wherein X is halogen (e.g., chloro, bromo), alkoxy, hydroxy, nitro, amine, or lower alkyl; with an electrophilic agent having the Formula III:

$$R^3 - L \qquad \text{III}$$

wherein L is a leaving group such as halogen (e.g., chlorobromo-, and so forth), sulfonate, sulfate, methylsulfonyloxy, p-toluenesulfonyloxy, quaternary amine, etc., and $R^3$ and Y are as defined herein.

This reaction is conducted in the presence of a base, such as alkali metal hydroxide such as sodium hydroxide, potassium t-butoxide or sodium methoxide, or other types such as sodium hydride or triphenyl methyl sodium.

Compounds of Formula III that may be utilized in the practice of the invention are perchloryl fluoride, trifluoromethyl bromide, cyanogen chloride, acetyl chloride, benzoyl chloride, ethyl bromo acetate, ethyl chloroformate, phenylsulfenyl chloride, pentafluoroethyl iodide, chlorine, bromine, methyl sulfenyl chloride, methyl thiomesylate, etc. Suitable organic solvents include benzene, dimethoxyethane, dimethyl sulfoxide, dioxane, dimethyl formamide, etc.

It is to be understood that the term lower alkyl and lower alkoxy in the formulae of the instant invention include straight and branched chain radicals of from 1 to about 8 carbons such as methyl, ethyl, propyl, isopropyl, butyl, isobutyl, t-butyl, amyl, methoxy, ethoxy, propoxy, isopropoxy, and the like. Further, it will be appreciated that certain of the compounds of this invention exist in different optically active forms. The various stereoisomeric forms as well as the racemic compounds are within the scope of this invention. The preferred form is that in which 6-amino group (or substituted 6-amino group) is cis to the sulfur atom, thereby resembling the natural cephalosporins.

The term aryl, such as in aryl, aryloxy, arylthio, etc. is intended to include phenyl, α- and β-naphthyl. In addition, the term aryl is intended to encompass mono and disubstituted-phenyl, or α- and β-naphthyl groups wherein said substituents are halogen, hydroxy, amino, nitro and alkyl.

The term "heterocyclyl", while intended to encompass the entire class, more specifically is intended to encompass the thiophene, isoxazole, oxadiazole, thiadiazole, pyridine, pyrazene, morpholine, quinoline, isoquinoline, tetrazole, furan, pyrrole and indole. The ring systems may be at various hydrogenated states, such as dihydrofuran and tetrahydrofuran. In addition, the point of linkage may be at any of the possible ring positions and the ring systems may carry additional substituents such as alkyl, alkoxy, amino, nitro, halogen, etc.

Suitable compounds of Formula II include any Schiff's base of 7-ADCA or 7-ACA (or a protected form thereof). When using this process, the preferred Schiff's bases are those formed with aldehydes which do not interfere with the substitution reaction. Thus, although any of the Schiff's bases of 6-APA disclosed in Patent Application No. 84,946 can be used correspondingly with 7-ACA or 7-ADCA nuclei, the preferred are those of the formula: RCHO, wherein R is phenyl, p-methoxyphenyl, m-nitrophenyl, halophenyl (e.g., p-chlorophenyl, m-fluorophenyl, and o-bromophenyl), (lower alkoxy) e.g., o-methoxyphenyl), carbo(lower alkoxy)phenyl (e.g., p-carbomethoxyphenyl, o-carboethoxyphenyl, p-carbohexyloxyphenyl, and m-carbobutoxyphenyl), o-n-propoxyphenyl, and p-n- hexyloxyphenyl), di(lower alkyl) aminophenyl [e.g., p-dimethylaminophenyl, o-diethylaminophenyl, p-(N-n-butyl-N-methylamine)-phenyl, and m-di-n-pentylaminophenyl], naphthyl. The reaction in forming compounds of Formula II is preferably conducted in an inert organic solvent for the Schiff's base reactant, such as methylene chloride, benzene, dimethoxyethane, dioxane and chloroform.

Compounds of the Formula II are used preferably in the form of an ester. Suitable esters include those formed with lower alkanols (e.g., methanol, ethanol and tert.-butanol), cycloalkanols (e.g., cyclohexanol and cyclopentanol), carbocyclic aryl aryl alcohols (e.g., benzyl alcohol, benzhydrol, 1-naphthylmethyl alcohol and 2-phenylethanol), trimethylsilyl, lower alkanoyl (lower alkanols) (e.g., hydroxyacetone and pivaloylmethanol), carbocyclic aroyl (lower alkanols) (e.g., benzoylmethanol, 2-benzoylethanol and 2-naphthylcarbonylmethanol), cycloalkylcarbonyl (lower alkanols) (e.g., hydroxymethylcyclohexylketone), lower alkanoyloxy (lower alkanols) (e.g., pivaloyloxymethanol), and substituted derivatives of any of the above, such as lower alkyl (e.g., methyl and ethyl), lower alkoxy (e.g., methoxy and butoxy), halo (e.g., chloro, fluoro and bromo), and nitro derivatives, as exemplified by 2,2,2-trichloroethanol, 2-bromoethanol, p-nitrophenol, p-methoxyphenol, p-methoxybenzyl alcohol, p,p'-dimethoxybenzhydrol, 2-dimethylamino ethanol, p-nitrobenzoylmethanol and p-methoxybenzoylmethanol.

The reaction of Compound II with Compound III yields a compound of Formula IV:

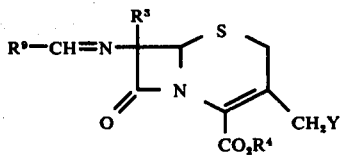

IV which can then be converted to compounds of Formula I by hydrolysis in the presence of a mild aqueous acid, such as hydrochloric, sulfuric, formic, trifluoroacetic, acetic and p-toluenesulfonic acid to yield the 7-substituted 7-aminocephalosporanic acid of Formula I.

In the event a 7-aryloxy compound is desired, an intermediate wherein $R^3$ = halogen such as fluorine, chlorine, or bromine is prepared, followed by mild solvolysis with phenol to produce IV, $R^3 = RO—$; there may then be hydrolyzed to corresponding compounds of Formula I. Similarly 7-alkoxy compounds can be made. In a similar manner, RZ may be introduced wherein R is lower alkyl, aryl or acyl and Z is oxygen, nitrogen or sulfur.

As stated above compounds of Formula I are valuable intermediates in the formation of acylated compounds having the Formula V:

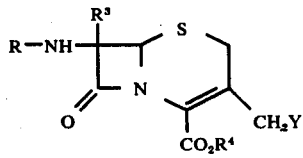

V wherein Y, $R^3$ and $R^4$ are as defined herein and R is acyl. Acyl in this invention is defined as:

a. $R^2(CH_2)_nCO—$ where $R^2$ is phenyl, nitrophenyl, chlorophenyl, bromophenyl, lower alkyl phenyl, lower alkoxy phenyl, cycloalkyl or heterocyclyl, and n is an integer from 0, 1 to 4, b. $R^5CO—$ where $R^5$ contains from 2 to 7 carbon atoms and is alkyl, alkylthioalkyl or alkoxyalkoxyalkyl, c. $R^6CO—$ where $R^6$ contains from 2 to 7 carbon atoms and is alkenyl, alkylthioalkenyl, alkenylthioalkyl, alkoxyalkenyl or alkenyloxyalkyl, d. $R^2X_1(CH_2)_nCO—$ where $R^2$ and n are as defined above and $X_1$ is oxygen or sulphur.

e. $R^2(CH_2)_nS(CH_2)_mCH_2CO—$ where $R^2$ and n are as defined above and m is 0 or an integer from 1 to 4, f. $R^2CO—$ where $R^2$ is as defined above, g. $R^7(CH_2)_nCO—$ where $R^7$ is carbocyclic or substituted carbocyclic (e.g., lower alkyl dihydrocyclohexyl, lower alkoxy dihydrocyclohexyl such as 2,4-dimethyl-2,4-dihydrocyclohexyl, and 2-propoxy-2,4-dihydrocyclohexyl), aryl, heterocyclyl, aryloxy, arylthio and alkyloxy, and n is an integer from 0, 1 to 4, h.

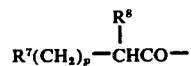

where $R^7$ is as defined herein, $R^8$ is alkyl, amino, ureido, carboxy, sulfonyl, phosphonyl, hydrogen, hydroxy, chloro, bromo, or iodo, p is an integer from 0, 1 to 3, and i.

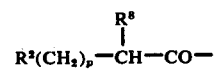

where $R^2$, $R^8$ and p are as defined above.

Compounds of general Formula V are prepared from compounds of general Formula I.

The formation of compounds of general Formula V may, for example, be effected by one of the following methods:

a. Reaction of the compound of general Formula I with an acid chloride, or acid anhydride, active ester, acid azide, etc. in aqueous or organic solution.

b. Reaction of the compound of general Formula I with a mixed anhydride of an acid corresponding to the desired acyl group and another acid, the mixed anhydride being formed by reaction of the acid corresponding to the desired acyl group with an alkyl haloformate, if desired formed in situ; the reaction with the mixed anhydride preferably being conducted in solution in an anhydrous, inert solvent in the presence of an acid binding agent e.g., a tertiary amine.

c. Reaction of the compound of Formula I with the activated form of a carboxylic acid formed by reaction with carbonyl-di-imidazole or dicyclohexylcarbodiimide or similar activating agent.

Alternatively, compounds of Formula IV may be acylated directly by the procedures of U.S. Patent Application 71,226, filed September 10, 1970, to yield compounds of Formula V directly where $R^4$ is hydrogen the procedure can be carried out by known methods.

The compounds of this invention have a broad spectrum of antibiotic activity. They have antibacterial activity against both gram-positive and gram-negative organisms, such as Staphylococcus aureus, Salmonella schottmuelleri, Proteus vulgaris, Escherichia coli and Streptococcus pyrogenes. They may be used as antibacterial agents in a prophylactic manner, e.g., in cleaning or disinfecting compositions, or otherwise to combat infections due to organisms such as those named above, and in general may be utilized in a manner similar to cephalothin, cephalexin, cephaloridine and other cephalosporins. For example, a compound of Formula I may be used in various animal species in an amount of about 0.1 to 100 mg/kg daily, orally or parenterally, in single or two to four divided doses to treat infections of bacterial origin. Up to about 600 mg. of a compound of Formula I or V may be incorporated in an oral dosage form such as tablets, capsules, or elixirs or an injectable form in a sterile aqueous vehicle prepared according to conventional pharmaceutical factors. In cleaning or disinfecting compositions, e.g., in farm or diary equipment, a concentration of about 0.01 to 1% by weight of such compounds admixed with, suspended or dissolved in conventional inert dry or aqueous carriers by application by washing or spraying may be utilized.

The following examples illustrate the invention (all temperatures being in degrees Centigrade, unless otherwise stated):

EXAMPLE 1

N-Benzylidene-7-Aminodesacetoxycephalosporanic acid, t-octylamine salt 25 g 7-aminodesacetoxycephalosporanic acid is slurried in 2.5 liters water and neutralized over a period of 1–1½ hours to pH 7.5 with octylamine. The solution clarified and 12.1 ml. benzaldehyde is added over a period of ½ hour. After two hours agitation at room temperature, the solids are filtered and washed with 100 ml. water. The product is dried at 40° C overnight to give 43 grams of the desired product.

EXAMPLES 2–5

By following the procedure of Example 1 and substituting in place of the benzaldehyde an equivalent amount of:

o-nitrobenzaldehyde,
m-chlorobenzaldehyde,
p-methoxybenzaldehyde, and
p-methylbenzaldehyde, the products obtained are:
N-o-nitrobenzylidene-7-aminodesacetoxycephalosporanic acid, t-octylamine salt;
N-m-chlorobenzylidene-7-aminodesacetoxycephalosporanic acid, t-octylamine salt;
N-p-methoxybenzylidene-7-aminodesacetoxycephalosporanic acid, t-octylamine salt; and
N-p-methylbenzylidene-7-aminodesacetoxycephalosporanic acid, t-octylamine salt.

EXAMPLE 6

N-Benzylidene-7-Aminodesacetoxycephalosporanic Acid 73.8 Mmoles N-benzylidene-7-aminodesacetoxycephalosporanic acid, t-octylamine salt is added to 240 ml. methylene chloride cooled to 0°–5° C. (water bath). After dispersion 158.5 mmoles benzaldehyde are added, followed by the addition of an 8 ml. tetrahydrofuran solution containing 76.2 mmoles trifluoroacetic acid. During the course of this addition, the reaction mixture gradually clarifies to finally form a clear, slightly yellow solution. The reaction mixture is allowed to reach room temperature and concentrated to one-third its volume in vacuo at a temperature not exceeding 30° C. On cooling the desired product crystallized out in 76 mole %.

EXAMPLE 7

Benzyl ester of N-benzylidene-7-aminodesacetoxycephalosporanic acid

Treatment of a 0.1 molar solution of N-benzylidene-7-aminodesacetoxycephalosporanic acid with one equivalent of phenyl diazomethane in ether (Overberger and Anselme, J. ORG. CHEM., 28, 592 [1963]; Idem, J. AM. CHEM. SOC., 86, 658 [1964] for one hour, followed by evaporation deposits the product.

EXAMPLE 8

Diphenylmethyl ester of N-benzylidene-7-aminodesacetoxycephalosporanic acid

Substitution of one equivalent of diphenyldiazomethane for the solution of phenyl diazomethane in Example 7 gives the desired product.

EXAMPLE 9

Trichloroethyl ester of 7-benzaliminodesacetoxycephalosporanic acid

The Schiff base of Example 1 (10.0 g) is dissolved in 150 ml. of dichloromethane containing pyridine (5.2 g). Trichloroethanol 9.84 g is added followed by 6.79 g dicyclohexylcarbodiimide and the mixture stirred for two hours at room temperature. Precipitation of dicyclohexylurea occurs quickly. After two hours the precipitate is filtered off. The filtrate is diluted with dichloromethane and washed twice with an equal volume of water, first at pH 3.5, then at pH 7.2. It is then washed with saturated sodium chloride, dried over anhydrous magnesium sulfate, and stripped to dryness in vacuo. Wt. of yellow oil = 13.2 g.

The product is crystallized by dissolving it in 5 ml. of ether and adding hexane to the warm solution until slightly turbid upon cooling.

EXAMPLE 10 p-Methoxybenzyl ester of 7-benzaliminodesacetoxycephalosporanic acid

Substitution of 9.1 grams of p-methoxybenzyl alcohol for trichloroethanol in Example 9 leads to the desired product.

EXAMPLE 11

Methyl ester of 7-benzaliminodesacetoxycephalosporanic acid

By treating a dioxane solution of the product of Example 2 with excess ethereal diazomethane, followed by evaporation of the solvent, the desired product is obtained. Trituration with hexane gives a powder.

EXAMPLE 12

7-Benzalimino-7-cyanodesacetoxycephalosporanic acid methyl ester 12.5 Meq. 7-benzaliminodesacetoxycephalosporanic acid methyl ester are dissolved in 2 ml. dry DME under nitrogen at −5° C. along with 12.5 meq. potassium t-butoxide. The reaction mixture turns yellow after a few minutes of stirring at that low temperature. 12.5 meq. of cyanogenchloride is added. After ½ hour the reaction mixture is diluted with chloroform, washed with water, dried over magnesium sulphate and evaporated in vacuo to give the product.

EXAMPLE 13

7-Benzalimino-7-cyanodesacetoxycephalosporanic acid, p-methoxybenzyl ester

Substitution of 12.5 meq. of the p-methoxybenzyl ester of 7-benzaliminodesacetoxycephalosporanic acid in Example 12 for the methyl ester leads to the desired product.

EXAMPLE 14

7-Cyano-7-aminodesacetoxycephalosporanic acid 0.2 Mmole N-benzylidene-7-amino-7-cyanodesacetoxycephalosporanic acid, p-methoxybenzyl ester are dissolved in 6.5 ml. benzene and 4.33 mmoles anisole and 7.6 mmoles TFA are added. The reaction is allowed to proceed at room temperature for 6 hours. The whole is concentrated under vacuum. The residue is washed with 20% ether/petroleum ether to leave 7-cyano-7-aminodesacetoxycephalosporanic acid.

EXAMPLE 15

7-Benzalimino-7-cyanodesacetoxycephalosporanic acid, benzyl ester

Substitution of 12.5 meq. of the benzyl ester of 7-benzaliminodesacetoxycephalosporanic acid in Example 12 for the methyl ester leads to the desired product.

EXAMPLE 16

7-Benzalimino-7-cyanodesacetoxycephalosporanic acid, benzhydryl ester

By substituting 12.5 meq. of the benzhydryl ester for the methyl ester of Example 12, the desired product is obtained.

EXAMPLE 17

7-Amino-7-cyanodesacetoxycephalosporanic acid, methyl ester 6.2 Meq. 7-benzalimino-7-cyanodesacetoxycephalosporanic acid, methyl ester are hydrolyzed in a 50:50 mixture of acetone and 0.1 N aqueous hydrochloric acid for 10 minutes. The reaction mixture is then diluted with water and washed with chloroform. The acidic layer is then basified and extracted with chloroform. This latter chloroform layer is dried over magnesium sulphate and evaporated to dryness in vacuo. To give 5 meq. 7-amino-7-cyano desacetoxycephalosporanic acid, methyl ester.

EXAMPLE 18

7-Amino-7-cyanodesacetoxycephalosporanic acid, p-methoxybenzyl ester

Substituting 6.2 meq. of the product of Example 13 and following the procedure of Example 17, the desired product is obtained.

EXAMPLE 19

7-Amino-7-cyanodesacetoxycephalosporanic acid, benzyl ester

Substituting 6.2 meq. of the product of Example 15 for the substrate of Example 17, and following the procedure therein, the desired product is obtained.

EXAMPLE 20

7-Amino-7-cyanodesacetoxycephalosporanic acid, benzhydryl ester

Substituting 6.2 meq. of the product of Example 16 for the substrate of Example 17, and following the procedure therein, the desired product is obtained.

EXAMPLE 21

7-Phenylacetamido-7-cyanodesacetoxycephalosporanic acid, methyl ester 3.25 Meq. 7-amino-7-cyanodesacetoxycephalosporanic acid, methyl ester are dissolved in 30 ml. chloroform, and cooled to ice-bath temperature under nitrogen. Then 3.25 meq. triethylamine are added followed by the addition of 3.25 meq. phenylacetylchloride. The reaction is allowed to proceed for two hours at ice-bath temperatures and under nitrogen. The solution is diluted with chloroform, washed with an aqueous solution at pH 7.2, washed with water, dried over magnesium sulphate, and evaporated to dryness to give 1.7 meq. of 7-phenylacetamido-7-cyanodesacetoxycephalosporanic acid, methyl ester as a clear oil.

EXAMPLE 22

7-Phenylacetamido-7-cyanodesacetoxycephalosporanic acid, p-methoxybenzyl ester a. Substituting 3.25 meq. of 7-amino-7-cyanodesacetoxycephalosporanic acid, p-methoxybenzyl ester in Example 21 for 7-amino-7-cyanodesacetoxycephalosporanic acid, methyl ester, and following the procedure therein, the desired product was obtained.

b. 7-Phenylacetamido-7-cyanodesacetoxycephalosporanic acid

Treatment of 7-phenylacetamido-7-cyanodesacetoxycephalosporanic acid, p-methoxybenzyl ester in benzene with 2.1 mmoles anisole and 3.5 mmoles trifluoroacetic acid for 6 hours. The desired product is extracted from the acid solution in good yield.

EXAMPLE 23

7-Benzalimino-7-(o-nitrophenylsulfenyl)desacetoxycephalosporanic acid, methyl ester 7-Benzalimino-7-(o-nitrophenylsulfenyl)desacetoxycephalosporanic acid, methyl ester is prepared by the procedure of Example 12, but using an equivalent amount of o-nitrophenylsulfenyl chloride in place of cyanogen chloride.

EXAMPLE 24

7-Amino-7-(o-nitrophenylsulfenyl)desacetoxycephalosporanic acid, methyl ester

7-Amino-7-benzyldesacetoxycephalosporanic acid, methyl ester is prepared by using the product of Example 23 to replace the substrate 7-cyano compound of Example 17.

EXAMPLE 25

7-Phenylacetamido-7-(o-nitrophenylsulfenyl)-desacetoxycephalosporanic acid, methyl ester 7-Phenylacetamido-7-(o-nitrophenylsulfenyl)-desacetoxycephalosporanic acid, methyl ester is prepared by using the product of Example 24 for the substrate in Example 21.

EXAMPLE 26

7-Phenylacetamido-7-(o-nitrophenylsulfenyl)-desacetoxycephalosporanic acid

7-Phenylacetamido-7-(o-nitrophenylsulfenyl)-desacetoxycephalosporanic acid is prepared from the methyl ester of Example 25, following the procedure of Example 22(b).

EXAMPLES 27–49

By following the procedures of Example 22 and substituting an equivalent amount of the corresponding acid chloride of the following carboxylic acids α-(2-chlorophenoxy)propionic acid,
α-(4-sulfamylphenoxy)-n-butyric acid,
α-(3,4-dimethoxyphenoxy)-n-pentanoic acid,
α-(3-methylphenoxy)isovaleric acid,
α-(3-methylthiophenoxy)propionic acid,
α-(4-dimethylaminophenoxy)-n-hexanoic acid,
α-(2-methoxyphenoxy)-n-decanoic acid,
α-(2,4-dichlorophenoxy)phenylacetic acid,
α-(2-nitrophenoxy)-β-phenylpropionic acid,
α-(2-acetamidophenoxy)-γ-phenylbutyric acid,
α-(2,4-dimethylphenoxy)-n-butyric acid,
α-(4-isopropylphenoxy)propionic acid,
α-(3-bromophenoxy)-n-butyric acid,
α-(2-iodophenoxy)phenylacetic acid,
α-(2-diethylaminophenoxy)isovaleric acid,
α-(3,5-dichlorophenoxy)isohexanoic acid,
α-(4-cyclohexylphenoxy)propionic acid,
α-phenoxy-isovaleric acid,
α-phenoxy-n-decanoic acid,
α-phenoxy-δ-phenylbutyric acid,
α-(2-benzylphenoxy)-n-butyric acid,
α-(2-trifluoromethylphenoxy)propionic acid, and
α-(4-fluorophenoxy)propionic acid, the products obtained are
  7-[α-(2-chlorphenoxy)propionamido]-7-cyanodesacetoxycephalosporanic acid,
  7-[α-(4-sulfamylphenoxy)-n-butyramido]-7-cyanodesacetoxycephalosporanic acid,
  7-[α-(3,4-dimethoxyphenoxy)n-pentanoamido]-7-cyanodesacetoxycephalosporanic acid,
  7-[α-(3-methylphenoxy)isovaleramido]-7-cyanodesacetoxycephalosporanic acid,
  7-[α-(4-methylthiophenoxy)propionamido]-7-cyanodesacetoxycephalosporanic acid,
  7-[α-(4-dimethylaminophenoxy)-n-hexanoamido]-7-cyanodesacetoxycephalosporanic acid,
  7-[α-(2-methoxyphenoxy)-n-decanoamido]-7-cyanodesacetoxycephalosporanic acid,
  7-[α-(2,4-dichlorophenoxy)phenylacetamido]-7-cyanodesacetoxycephalosporanic acid,
  7-[α-(2-nitrophenoxy)-β-phenylpropionamido]-7-cyanodesacetoxycephalosporanic acid,
  7-[α-(2-acetamidophenoxy)-δ-phenylbutyramido]-7-cyanodesacetoxycephalosporanic acid,
  7-[α-(2,4-dimethylphenoxy)-n-butyramido]-7-cyanodesacetoxycephalosporanic acid,
  7-[α-(4-isopropylphenoxy)propionamido]-7-cyanodesacetoxycephalosporanic acid,
  7-[α-(3-bromophenoxy)-n-butyramido]-7-cyanodesacetoxycephalosporanic acid,
  7-[α-(2-iodophenoxy)phenylacetamido]-7-cyanodesacetoxycephalosporanic acid,
  7-[α-(2-diethylaminophenoxy)isovaleramido]-7-cyanodesacetoxycephalosporanic acid,
  7-[α-(3,5-dichlorophenoxy)isohexanoamido]-7-cyanodesacetoxycephalosporanic acid,
  7-[α-(4-cyclohexylphenoxy)propionamido]-7-cyanodesacetoxycephalosporanic acid,
  7-[α-phenoxy-isovaleramido]-7-cyanodesacetoxycephalosporanic acid,
  7-[α-phenoxy-n-decanoamido]-7-cyanodesacetoxycephalosporanic acid,
  7-[α-phenoxy-δ-phenylbutyramido]-7-cyanodesacetoxycephalosporanic acid,
  7-[α-(2-benzylphenoxy)-n-butyramido]-7-cyanodesacetoxycephalosporanic acid,
  7-[α-(2-trifluoromethylphenoxy)propionamido]-7-cyanodesacetoxycephalosporanic acid, and
  7-[α-(4-fluorophenoxy)propionamido]-7-cyanodesacetoxycephalosporanic acid, respectively.

EXAMPLES 50–79

By following the procedures of Example 22 and substituting an equivalent amount of the corresponding acid chloride of the following carboxylic acids α-phenylthiopropionic acid,
α-paranitrophenylthiopropionic acid,
-parachlorophenylthiopropionic acid,
α-phenylthiobutyric acid,
α-phenylthiocaproic acid,
α-phenylthioisovaleric acid,
α-(4-t-butylphenylthio)propionic acid,
α-ortho-tolythiopropionic acid,
α-ortho-nitrophenylthiopropionic acid,
α-parachlorophenylthiobutyric acid,
α-(3,4,5-trichlorophenylthio)propionic acid,
α-(3-trifluoromethylphenylthio)butyric acid,
α-parabromophenylthioisovaleric acid,
α-paraphenylphenylthiopropionic acid,
α-(4-methoxyphenylthio)caproic acid,
α-(4-cyclohexylphenylthio)butyric acid,
α-phenylthio-α-cyclohexylacetic acid,
α-(2,4-dichlorophenylthio)caproic acid,
α-(2,4-diisoamylphenylthio)propionic acid,
α-(4-benzylphenylthio)propionic acid,
α-(4-sulfamylphenylthio)butyric acid,
α-(2-allyloxyphenylthio)propionic acid,
α-(4-allylphenylthio)isovaleric acid,
α-(4-dimethylaminophenylthio)propionic acid,
α-(2,5-dichlorophenylthio)butyric acid,
α-(2-iodophenylthio)propionic acid,
α-(2-acetamidophenylthio)propionic acid,
α-(4-diethylaminophenylthio)propionic acid, and
α-(3-fluorophenylthio)butyric acid, the products obtained are:
  7-(α-phenylthiopropionamido)-7-cyanodesacetoxycephalosporanic acid,
  7-(α-paranitrophenylthiopropionamido)-7-cyanodesacetoxycephalosporanic acid, 7-(α-parachlorophenylthiopropionamido)-7-cyanodesacetoxycephalosporanic acid,
7-(α-phenylthiobutyramido)-7-cyanodesacetoxycephalosporanic acid,
7-(α-phenylthiocaproamido)-7-cyanodesacetoxycephalosporanic acid
7-(α-phenylthioisovaleramido)-7-cyanodesacetoxycephalosporanic acid,
7-[α-(4-t-butylphenylthio)propionamido]-7-cyanodesacetoxycephalosporanic acid,
7-[α-ortho-tolythiopropionamido]-7-cyanodesacetoxycephalosporanic acid,
7-(α-ortho-nitrophenylthiopropionamido)-7-cyanodesacetoxycephalosporanic acid,
7-(α-parachlorophenylthiobutyramido)-7-cyanodesacetoxycephalosporanic acid,
7-[α-(3,4,5-trichlorophenylthio)propionamido]-7-cyanodesacetoxycephalosporanic acid,
7-[α-(3-trifluoromethylphenylthio)butyramido]-7-cyanodesacetoxycephalosporanic acid,
7-(α-parabromophenylthioisovaleramido)-7-cyanodesacetoxycephalosporanic acid,
7-(α-paraphenylphenylthiopropionamido)-7-cyanodesacetoxycephalosporanic acid,
7-[α-(4-methoxyphenylthio)caproamido]-7-cyanodesacetoxycephalosporanic acid
7-[α-(4-cyclohexylphenylthio)butyramido]-7-cyanodesacetoxycephalosporanic acid,
7(α-phenylthio-α--cyclohexylacetamido)-7-cyanodesacetoxycephalosporanic acid,
7-[α-(2,4-dichlorophenylthio)caproamido]-7-cyanodesacetoxycephalosporanic acid,
7-[α-(2,4-diisoamylphenylthio)propionamido]-7-cyanodesacetoxycephalosporanic acid,
7-[α-(4-benzylphenylthio)propionamido]-7-cyanodesacetoxycephalosporanic acid,
7-[α-(4-sulfamylphenylthio)butyramido]-7-cyanodesacetoxycephalosporanic acid,
7-[α-(2-allyloxyphenylthio)propionamido]-7-cyanodesacetoxycephalosporanic acid,
7-[α-(4-allylphenylthio)isovaleramido]-7-cyanodesacetoxycephalosporanic acid,
7-[α-(4-dimethylaminophenylthio)propionamido]-7-cyanodesacetoxycephalosporanic acid,
7-[α-(2,5-dichlorophenylthio)butyramido]-7-cyanodesacetoxycephalosporanic acid,
7-[α-(2-iodophenylthio)propionamido]-7-cyanodesacetoxycephalosporanic acid,
7-[α-(2-acetamidophenylthio)propionamido]-7-cyanodesacetoxycephalosporanic acid,
7-[α-(4-diethylaminophenylthio)propionamido]-7-cyanodesacetoxycephalosporanic acid,
7-[α-(3-fluorophenylthio)butyramido]-7-cyanodesacetoxycephalosporanic acid, respectively.

EXAMPLES 80-93

By following the procedures of Example 22 and substituting an equivalent amount of the corresponding acid chloride of the following carboxylic acids D,L-α-amino-(3-thienyl)acetic acid,
α-amino-(5-ethyl-2-thienyl)acetic acid,
α-amino-(5-methyl-2-thienyl)acetic acid,
α-amino-(5-t-butyl-2-thienyl)acetic acid,
α-amino-(2,5-dimethyl-3-thienyl)acetic acid,
α-amino-(5-chloro-2-thienyl)acetic acid,
α-amino-(5-bromo-2-thienyl)acetic acid,
α-amino-(5-phenyl-3-chloro-2-thienyl)acetic acid,
α-amino-(3,5-dimethyl-2-thienyl)acetic acid,
α-amino-(5-cyclohexyl-2-thienyl)acetic acid,
α-amino-(5-diethylamino-2-thienyl)acetic acid,
α-amino-(4-methylsulfonyl-2-thienyl)acetic acid,
α-amino-(3-ethylthio-2-thienyl)acetic acid, and
α-amino-(4-cycloheptyloxy-2-thienyl)acetic acid,
the products obtained are
D,L-7-[α-amino-(3-thienyl)acetamido]-7-cyanodesacetoxycephalosporanic acid,
7-[α-amino-(5-ethyl-2-thienyl)acetamido]-7-cyanodesacetoxycephalosporanic acid,
7-[α-amino-(5-methyl-2-thienyl)acetamido]-7-cyanodesacetoxycephalosporanic acid,
7-[α-amino-(5-t-butyl)-2-thienyl)acetamido]-7-cyanodesacetoxycephalosporanic acid,
7-[α-amino-(2,5-dimethyl-3-thienyl)acetamido]-7-cyanodesacetoxycephalosporanic acid,
7-[α-amino-(5-chloro-2-thienyl)acetamido]-7-cyanodesacetoxycephalosporanic acid,
7-[α-amino-(5-bromo-2-thienyl)acetamido]-7-cyanodesacetoxycephalosporanic acid,
7-[α-amino-(5-phenyl-3-chloro-2-thienyl)acetamido]-7-cyanodesacetoxycephalosporanic acid,
7-[α-amino-(3,5-dimethyl-2-thienyl)acetamido]-7-cyanodesacetoxycephalosporanic acid,
7-[α-amino-(5-cyclohexyl-2-thienyl)acetamido]-7-cyanodesacetoxycephalosporanic acid,
7-[α-amino-(5-diethylamino-2-thienyl)acetamido]-7-cyanodesacetoxycephalosporanic acid,
7-[α-amino-(4-methylsulfonyl-2-thienyl)acetamido]-7-cyanodesacetoxycephalosporanic acid,
7-[α-amino-(3-ethylthio-2-thienyl)acetamido]-7-cyano-desacetoxycephalosporanic acid,
7-[α-amino-(4-cycloheptyloxy-2-thienyl)acetamido]-7-cyanodesacetoxycephalosporanic acid, respectively.

EXAMPLE 94-116

By following the procedures of Example 22 and substituting an equivalent amount of the corresponding acid chloride of the following carboxylic acids α-amino-p-chlorophenylacetic acid,
α-amino-p-methoxyphenylacetic acid,
L-(+)-α-aminophenylacetic acid,
α-amino-4-diethylaminophenylacetic acid,
α-amino-4-trifluoromethylphenylacetic acid,
α-amino-2,4-dibromophenylacetic acid,
α-amino-2-nitrophenylacetic acid,
α-amino-3-methylphenylacetic acid,
α-amino-4-sulfamylphenylacetic acid,
α-amino-2-iodophenylacetic acid,
α-amino-4-t-butylphenylacetic acid,
α-amino-2-acetamidophenylacetic acid,
α-amino-3-nitrophenylacetic acid,
α-amino-3,4-dimethoxyphenylacetic acid,
α-amino-4-dimethylaminophenylacetic acid,
α-amino-2,4-dichlorophenylacetic acid,
α-amino-4-isopropylphenylacetic acid,
α-amino-3-bromophenylacetic acid,
α-amino-3-iodophenylacetic acid,
α-amino-2-diethylaminophenylacetic acid,
α-amino-2-trifluoromethylphenylacetic acid,
α-amino-4-fluorophenylacetic acid, and
α-amino-3,4,5-trifluoromethylphenylacetic acid, the products obtained are
7-(α-amino-p-chlorophenylacetamido)-7-cyanodesacetoxycephalosporanic acid,
7-(α-amino-p-methoxyphenylacetamido)-7-cyanodesacetoxycephalosporanic acid,
7-[L-(+)-α-aminophenylacetamido]-7-cyanodesacetoxy cephalosporanic acid,
7-(α-amino-4-diethylaminophenylacetamido)-7-cyanodesacetoxycephalosporanic acid,
7-(α-amino-4-trifluoromethylphenylacetamido)-7-cyanodesacetoxycephalosporanic acid,
7-(α-amino-2,4-dibromophenylacetamido)-7-cyanodesacetoxycephalosporanic acid,
7-(α-amino-2-nitrophenylacetamido)-7-cyanodesacetoxycephalosporanic acid,
7-(α-amino-3-methylphenylacetamido)-7-cyanodesacetoxycephalosporanic acid,
7-(α-amino-4-sulfamylphenylacetamido)-7-cyanodesacetoxycephalosporanic acid,
7-(α-amino-2-iodophenylacetamido)-7-cyanodesacetoxycephalosporanic acid,
7-(α-amino-4-t-butylphenylacetamido)-7-cyanodesacetoxycephalosporanic acid,
7-(α-amino-2-acetamidophenylacetamido)-7-cyanodesacetoxycephalosporanic acid,
7-(α-amino-3-nitrophenylacetamido)-7-cyanodesacetoxycephalosporanic acid ,
7-(α-amino-3,4-dimethoxyphenylacetamido)-7-cyanodesacetoxycephalosporanic acid,
7-(α-amino-4-dimethylaminophenylacetamido)-7-cyanodesacetoxycephalosporanic acid,
7-(α-amino-2,4-dichlorophenylacetamido)-7-cyanodesacetoxycephalosporanic acid,
7-(α-amino-4-isopropylphenylacetamido)-7-cyanodesacetoxycephalosporanic acid,
7-(α-amino-3-bromophenylacetamido)-7-cyanodesacetoxycephalosporanic acid,
7-(α-amino-3-iodophenylacetamido)-7-cyanodesacetoxycephalosporanic acid,
7-(α-amino-2-diethylaminophenylacetamido)-7-cyanodesacetoxycephalosporanic acid,
7-(α-amino-2-trifluoromethylphenylacetamido)-7-cyanodesacetoxycephalosporanic acid,
7-(α-amino-4-fluorophenylacetamido)-7-cyanodesacetoxycephalosporanic acid, and
7-(α-amino-3,4,5-trifluoromethylphenylacetamido)-7-cyanodesacetoxycephalosporanic acid, respectively.

EXAMPLES 117–187

By following the procedures of Example 22 and substituting an equivalent amount of the corresponding acid choride: benzoyl chloride, 3,5-dinitrobenzoyl chloride,
2-chlorobenzoyl chloride,
2-methylbenzoyl chloride,
4-aminobenzoyl chloride,
4-nitrobenzoyl chloride,
4-hydroxybenzoyl chloride,
3,4,5-trimethoxybenzoyl chloride,
4-methylbenzoyl chloride,
4-chlorobenzoyl chloride,
3,4-dichlorobenzoyl chloride,
3-nitrobenzoyl chloride,
2,4,6-trimethoxybenzoyl chloride,
2-hydroxybenzoyl chloride,
4-ethoxybenzoyl chloride,
2,6-dimethoxybenzoyl chloride,
2,4,6-trimethylbenzoyl chloride,
2,6-dichlorobenzoyl chloride,
2,6-diethoxybenzoyl chloride,
2,6-di-n-butyoxybenzoyl chloride,
2,6-dibenzyloxybenzoyl chloride,
2,3,6-trimethoxybenzoyl chloride,
2,4,6-tribromobenzoyl chloride,
2,6-di-n-propoxybenzoyl chloride,
2,6-dimethoxy-4-methylbenzoyl chloride,
4,6-diethyl-2-methoxybenzoyl chloride,
6-ethoxy-2-methoxybenzoyl chloride,
2-methylthiobenzoyl chloride,
2-benzylthiobenzoyl chloride,
2-phenoxybenzoyl chloride,
2-phenylbenzoyl chloride,
2-methoxybenzoyl chloride,
4-sulfamylbenzoyl chloride,
3,4-dimethoxybenzoyl chloride,
4-methoxybenzoyl chloride,
3-methylbenzoyl chloride,
3-dimethylaminobenzoyl chloride,
2-methoxybenzyl chloride,
2-chloro-3,4,5-trimethoxybenzoyl chloride,
2,4-dichlorobenzoyl chloride,
2-nitrobenzoyl chloride,
4-methylaminobenzoyl chloride,
2-acetamidobenzoyl chloride,
2,4-dimethylbenzoyl chloride,
2,4,5-trimethylbenzoyl chloride,
4-isopropylbenzoyl chloride,
3-bromobenzoyl chloride,
2-iodobenzoyl chloride,
2-ethylaminobenzoyl chloride,
2,5-dihydroxybenzoyl chloride,
4-hydroxy-3-methoxybenzoyl chloride,
4-allylbenzoyl chloride,
4allyloxybenzoyl chloride,
2-trifluoromethylbenzoyl chloride,
4-fluorobenzoyl chloride,
2-phenylthiobenzoyl chloride,
2-benzylbenzoyl chloride,
2,6-dihydroxybenzoyl chloride,
2,6-diacetoxybenzoyl chloride,
2,6-dimethylthiobenzoyl chloride,
2,4,6trinitrobenzoyl chloride,
2,6-diacetamidobenzoyl chloride,
2,6-dibromobenzoyl chloride,
2,6-dimethylbenzoyl chloride,
2,6-diethylbenzoyl chloride,
2,6-diisopropylbenzoyl chloride,
2,6-diallyloxybenzoyl chloride,
3-bromo-2,6-dimethoxybenzoyl chloride,
4-chloro-2,6-dimethoxybenzoyl chloride,
2-chloro-6-nitrobenzoyl chloride, and
2-hydroxy-6-methoxybenzoyl chloride,
the products obtained are
7-(benzamido)-7-cyanodesacetoxycephalosporanic acid,
7-(3,5-dinitrobenzamido)-7-cyanodesacetoxycephalosporanic acid,
7-(2-chlorobenzamido)-7-cyanodesacetoxycephalosporanic acid,
7-(2-methylbenzamido)-7-cyanodesacetoxycephalosporanic acid,
7-(4-aminobenzamido)-7-cyanodesacetoxycephalosporanic acid, 7-(4-nitrobenzamido)-7-cyanodesacetoxycephalosporanic acid,
7-(4-hydroxybenzamido)-7-cyanodesacetoxycephalosporanic acid,
7-(3,4,5-trimethoxybenzamido)-7-cyanodesacetoxycephalosporanic acid,
7-(4-methylbenzamido)-7-cyanodesacetoxycephalosporanic acid,
7-(4-chlorobenzamido)-7-cyanodesacetoxycephalosporanic acid,
7-(3,4-dichlorobenzamido)-7-cyanodesacetoxycephalosporanic acid,
7-(3-nitrobenzamido)-7-cyanodesacetoxycephalosporanic acid,
7-(2,4,6-trimethoxybenzamido)-7-cyanodesacetoxycephalosporanic acid,
7-(2-hydroxybenzamido)-7-cyanodesacetoxycephalosporanic acid,
7-(4-ethoxybenzamido)-7-cyanodesacetoxycephalosporanic acid,
7-(2,6-dimethoxybenzamido)-7-cyanodesacetoxycephalosporanic acid,
7-(2,4,6-trimethylbenzamido)-7-cyanodesacetoxycephalosporanic acid,
7-(2,6-dichlorobenzamido)-7-cyanodesacetoxycephalosporanic acid,
7-(2,6-diethoxybenzamido)-7-cyanodesacetoxycephalosporanic acid,
7-(2,6-di-n-butoxybenzamido)-7-cyanodesacetoxycephalosporanic acid,
7-(2,6-dibenzyloxybenzamido)-7-cyanodesacetoxycephalosporanic acid,
7-(2,3,6-trimethoxybenzamido)-7-cyanodesacetoxycephalosporanic acid,
7-(2,4,6-tribromobenzamido)-7-cyanodesacetoxycephalosporanic acid,
7-(2,6-di-n-propoxybenzamido)-7-cyanodesacetoxycephalosporanic acid,
7-(2,6-dimethoxy-4-methylbenzamido)-7-cyanodesacetoxycephalosporanic acid,
7-(4-6-diethyl-2-methoxybenzamido)-7-cyanodesacetoxycephalosporanic acid,
7-(6-ethoxy-2-methoxybenzamido)-7-cyanodesacetoxycephalosporanic acid,
7-(2-methylthiobenzamido)-7-cyanodesacetoxycephalosporanic acid,
7-(2-benzylthiobenzamido)-7-cyanodesacetoxycephalosporanic acid,
7-(2-phenoxybenzamido)-7-cyanodesacetoxycephalosporanic acid,
7-(2-phenylbenzamido)-7-cyanodesacetoxycephalosporanic acid,
7-(2-methoxybenzamido)-7-cyanodesacetoxycephalosporanic acid,
7-(4-sulfamylbenzamido)-7-cyanodesacetoxycephalosporanic acid,
7-(3,4-dimethoxybenzamido)-7-cyanodesacetoxycephalosporanic acid,
7-(4-methoxybenzamido)-7-cyanodesacetoxycephalosporanic acid,
7-(3-methylbenzamido)-7-cyanodesacetoxycephalosporanic acid,
7-(3-dimethylaminobenzamido)-7-cyanodesacetoxycephalosporanic acid,
7-(2-methoxybenzamido)-7-cyanodesacetoxycephalosporanic acid,
7-(2-chloro-3,4,5-trimethoxybenzamido)-7-cyanodesacetoxycephalosporanic acid,
7-(2,4-dichlorobenzamido)-7-cyanodesacetoxycephalosporanic acid,
7-(2-nitrobenzamido)-7-cyanodesacetoxycephalosporanic acid,
7-(4-methylaminobenzamido)-7-cyanodesacetoxycephalosporanic acid,
7-(2-acetamidobenzamido)-7-cyanodesacetoxycephalosporanic acid,
7-(2,4-dimethylbenzamido)-7-cyanodesacetoxycephalosporanic acid,
7-(2,4,5-trimethylbenzamido)-7-cyanodesacetoxycephalosporanic acid,
7-(4-isopropylbenzamido)-7-cyanodesacetoxycephalosporanic acid,
7-(3-bromobenzamido)-7-cyanodesacetoxycephalosporanic acid,
7-(2-iodobenzamido)-7-cyanodesacetoxycephalosporanic acid,
7-(2-ethylaminobenzamido)-7-cyanodesacetoxycephalosporanic acid,
7-(2,5-dihydroxybenzamido)-7-cyanodesacetoxycephalosporanic acid,
7-(4-hydroxy-3-methoxybenzamido)-7-cyanodesacetoxycephalosporanic acid,
7-(4-allylbenzamido)-7-cyanodesacetoxycephalosporanic acid,
7-(4-allyloxybenzamido)-7-cyanodesacetoxycephalosporanic acid,
7-(2-trifluoromethylbenzamido)-7-cyanodesacetoxycephalosporanic acid,
7-(4-fluorobenzamido)-7-cyanodesacetoxycephalosporanic acid,
7-(2-phenylthiobenzamido)-7-cyanodesacetoxycephalosporanic acid,
7-(2-benzylbenzamido)-7-cyanodesacetoxycephalosporanic acid,
7-(2,6-dihydroxybenzamido)-7-cyanodesacetoxycephalosporanic acid,
7-(2,6-diacetoxybenzamido)-7-cyanodesacetoxycephalosporanic acid,
7-(2,6-dimethylthiobenzamido)-7-cyanodesacetoxycephalosporanic acid,
7-(2,4,6-trinitrobenzamido)-7-cyanodesacetoxycephalosporanic acid,
7-(2,6-diacetamidobenzamido)-7-cyanodesacetoxycephalosporanic acid,
7-(2,6-dibromobenzamido)-7-cyanodesacetoxycephalosporanic acid,
7-(2,6-dimethylbenzamido)-7-cyanodesacetoxycephalosporanic acid,
7-(2,6-diethylbenzamido)-7-cyanodesacetoxycephalosporanic acid,
7-(2,6-diisopropylbenzamido)-7-cyanodesacetoxycephalosporanic acid,
7-(2,6-diallyloxybenzamido)-7-cyanodesacetoxycephalosporanic acid,
7-(3-bromo-2,6-dimethoxybenzamido)-7-cyanodesacetoxycephalosporanic acid,
7-(4-chloro-2,6-dimethoxybenzamido)-7-cyanodesacetoxycephalosporanic acid,
7-(2-chloro-6-nitrobenzamido)-7-cyanodesacetoxycephalosporanic acid,
7-(2-hydroxy-6-methoxybenzamido)-7-cyanodesacetoxycephalosporanic acid, respectively.

EXAMPLES 188–198

By following the procedures of Example 22 and substituting an equivalent amount of the corresponding acid chloride:

(4-nitrophenyl)acetyl chloride,
(4-bromophenyl)acetyl chloride,
(4-t-butylphenyl)acetyl chloride,
(4-trifluoromethylphenyl)acetyl chloride,
(3-fluorophenyl)acetyl chloride,
(4-sulfamylphenyl)acetyl chloride,
(2-benzylphenyl)acetyl chloride,
(3-methoxyphenyl)acetyl chloride,
(2-iodophenyl)acetyl chloride,
(3-diethylaminophenyl)acetyl chloride, and
(2,4-diisoamylphenyl)acetyl chloride, the product obtained are
7-[α-(4-nitrophenyl)acetamido]-7-cyanodesacetoxycephalosporanic acid,
7-[α-(4-bromophenyl)acetamido]-7-cyanodesacetoxycephalosporanic acid,
7-[α-(4-t-butylphenyl)acetamido]-7-cyanodesacetoxycephalosporanic acid,
7-[α-(4-trifluoromethylphenyl)acetamido]-7-cyanodesacetoxycephalosporanic acid,
7-[α-(3-fluorophenyl)acetamido]-7-cyanodesacetoxycephalosporanic acid,
7-[α-(4-sulfamylphenyl)acetamido]-7-cyanodesacetoxycephalosporanic acid,
7-[α-(2-benzylphenyl)acetamido]-7-cyanodesacetoxycephalosporanic acid,
7-[α-(3-methoxyphenyl)acetamido]-7-cyanodesacetoxycephalosporanic acid,
7-[α-(2-iodophenyl)acetamido]-7-cyanodesacetoxycephalosporanic acid,
7-[α-(3-diethylaminophenyl)acetamido]-7-cyanodesacetoxycephalosporanic acid, and
7-[α-(2,4-diisoamylphenyl)acetamido]-7-cyanodesacetoxycephalosporanic acid, respectively.

EXAMPLES 199–246

By following the procedures of Example 22 and substituting an equivalent amount of the corresponding acid chloride:

3-m-chlorophenyl-5-methyl-4-isoxazole-4-carbonyl chloride,
3-(2,4-dichlorophenyl)-5-methyl-4-isoxazole-4-carbonyl chloride,
3-(3,4-dichlorophenyl)-5-methyl-4-isoxazole-4-carbonyl chloride,
3-p-tolyl-5-methyl-4-isoxazole-4-carbonyl chloride,
3-o-nitrophenyl-5-methyl-4-isoxazole-4-carbonyl chloride,
3-m-nitrophenyl-5-methyl-4-isoxazole-4-carbonyl chloride,
3-p-nitrophenyl-5-methyl-4-isoxazole-4-carbonyl chloride,
3-p-bromophenyl-5-methyl-4-isoxazole-4-carbonyl chloride
3-p-fluorophenyl-5-methyl-4-isoxazole-4-carbonyl chloride,
3-p-methylsulfonylphenyl-5-methyl-4-isoxazole-4-carbonyl chloride,
3-p-methoxyphenyl-5-methyl-4-isoxazole-4-carbonyl chloride,
3-p-trifluoromethylphenyl-5-methyl-4-isoxazole-4-carbonyl chloride,
3-o-methoxyphenyl-5-methyl-4-isoxazole-4-carbonyl chloride,
3-p-ethoxyphenyl-5-methyl-4-isoxazole-4-carbonyl chloride,
3-(3,4-dimethoxyphenyl)-5-methyl-4-isoxazole-4-carbonyl chloride,
3-p-dimethylaminophenyl-5-methyl-4-isoxazole-4-carbonyl chloride,
3α-naphthyl-5-methyl-4-isoxazole-4-carbonyl chloride,
3-β-naphthyl-5-methyl-4-isoxazole-4-carbonyl chloride,
3-phenyl-5-ethyl-4-isoxazole-4-carbonyl chloride,
3-p-chlorophenyl-5-ethyl-4-isoxazole-4-carbonyl chloride,
3-phenyl-5-isopropyl-4-isoxazole-4-carbonyl chloride,
3-phenyl-5-methylmercapto-4-isoxazole-4-carbonyl chloride,
3-methyl-5-o-chlorophenyl-4-isoxazole-4-carbonyl chloride,
3-methyl-5-p-bromophenyl-4-isoxazole-4-carbonyl chloride,
3-methyl-5-o-iodophenyl-4-isoxazole-4-carbonyl chloride,
3-methyl-5-(2,4-dichlorophenyl)-4-isoxazole-4-carbonyl chloride,
3-methyl-5-m-nitrophenyl-4-isoxazole-4-carbonyl chloride,
3-methyl-5-p-tolyl-4-isoxazole-4-carbonyl chloride,
3-methyl-5-p-nitrophenyl-4-isoxazole-4-carbonyl chloride,
3-methyl-5-p-methoxyphenyl-4-isoxazole-4-carbonyl chloride,
3-methyl-5-p-ethoxyphenyl-4-isoxazole-4-carbonyl chloride,
3-methyl-5-(2,6-dimethoxyphenyl)-4-isoxazole-4-carbonyl chloride,
3-methyl-5-p-methylsulfonylphenyl-4-isoxazole-4-carbonyl chloride,
3-methyl-5-p-fluorophenyl-4-isoxazole-4-carbonyl chloride,
3-methyl-5-p-cyanophenyl-4-isoxazole-4-carbonyl chloride,
3-methyl-5-p-methylmercaptophenyl-4-isoxazole-4-carbonyl chloride,
3-methyl-5-p-dimethylaminophenyl-4-isoxazole-4-carbonyl chloride,
3-methyl-5-α-naphthyl-4-isoxazole-4-carbonyl chloride,
3-methyl-5-β-naphthyl-4-isoxazole-4-carbonyl chloride,
3-ethyl-5-phenyl-4-isoxazole-4-carbonyl chloride,
3-ethyl-5-p-chlorophenyl-4-isoxazole-4-carbonyl chloride,
3-isopropyl-5-phenyl-4-isoxazole-4-carbonyl chloride,
3-tert. butyl-5-methyl-4-isoxazole-4-carbonyl chloride,
3-methyl-5-p-trifluoromethylphenyl-4-isoxazole-4-carbonyl chloride,
3-methyl-5-cyclohexyl-4-isoxazole-4-carbonyl chloride,
3-cyclohexyl-5-methyl-4-isoxazole-4-carbonyl chloride,
3-α-furyl-5-methyl-4-isoxazole-4-carbonyl chloride, and
3-α-thienyl-5-methyl-4-isoxazole-4-carbonyl chloride, the products obtained are 3-m-chlorophenyl-5-methyl-4-isoxazolylcarbonylamino-7-cyanodesacetoxycephalosporanic acid,
3-(2,4-dichlorophenyl)-5-methyl-4-isoxazolylcarbonylamino-7-cyanodesacetoxycephalosporanic acid,
3-(3,4-dichlorophenyl)-5-methyl-4-isoxazolylcarbonylamino-7-cyanodesacetoxycephalosporanic acid,
3-p-tolyl-5-methyl-4-isoxazolylcarbonylamino-7-cyanodesacetoxycephalosporanic acid,
3-o-nitrophenyl-5-methyl-4-isoxazolylcarbonylamino-7-cyanodesacetoxycephalosporanic acid,
3-m-nitrophenyl-5-methyl-4-isoxazolylcarbonylamino-7-cyanodesacetoxycephalosporanic acid,
3-p-nitrophenyl-4-methyl-4-isoxazolylcarbonylamino-7-cyanodesacetoxycephalosporanic acid,
3-p-bromophenyl-5-methyl-4-isoxazolylcarbonylamino-7-cyanodesacetoxycephalosporanic acid,
3-p-fluorophenyl-5-methyl-4-isoxazolylcarbonylamino-7-cyanodesacetoxycephalosporanic acid,
3-p-methylsulfonylphenyl-5-methyl-4-isoxazolylcarbonylamino-7-cyanodesacetoxycephalosporanic acid,
3-p-methoxyphenyl-5-methyl-4-isoxazolylcarbonylamino-7 -cyanodesacetoxycephalosporanic acid,
3-p-trifluoromethylphenyl-5-methyl-4-isoxazolylcarbonylamino-7-cyanodesacetoxycephalosporanic acid,
3-o-methoxyphenyl-5-methyl-4-isoxazolylcarbonylamino-7-cyanodesacetoxycephalosporanic acid,
3-p-ethoxyphenyl-5-methyl-4-isoxazolylcarbonylamino-7-cyanodesacetoxycephalosporanic acid,
3-(3,4-dimethoxyphenyl)-5-methyl-4-isoxazolylcarbonylamino-7-cyanodesacetoxycephalosporanic acid,
3-p-dimethylaminophenyl-5-methyl-4-isoxazolylcarbonylamino-7-cyanodesacetoxycephalosporanic acid,
3-α-naphthyl-5-methyl-4-isoxazolylcarbonylamino-7-cyanodesacetoxycephalosporanic acid,
3-β-naphthyl-5-methyl-4-isoxazolylcarbonylamino-7-cyanodesacetoxycephalosporanic acid,
3-phenyl-5-ethyl-4-isoxazolylcarbonylamino-7-cyanodesacetoxycephalosporanic acid,
3-p-chlorophenyl-5-ethyl-4-isoxazolylcarbonylamino-7-cyanodesacetoxycephalosporanic acid,
3-phenyl-5-isopropyl-4-isoxazolylcarbonylamino-7-cyanodesacetoxycephalosporanic acid,
3-phenyl-5-methylmercapto-4-isoxazolylcarbonylamino-7-cyanodesacetoxycephalosporanic acid,
3-methyl-5-o-chlorophenyl-4-isoxazolylcarbonylamino-7-cyanodesacetoxycephalosporanic acid,
3-methyl-5-p-bromophenyl-4-isoxazolylcarbonylamino-7-cyanodesacetoxycephalosporanic acid,
3-methyl-5-o-iodophenyl-4-isoxazolylcarbonylamino-7-cyanodesacetoxycephalosporanic acid,
3-methyl-5-m-nitrophenyl-4-isoxazolylcarbonylamino-7-cyanodesacetoxycephalosporanic acid,
3-methyl-5-p-tolyl-4-isoxazolylcarbonylamino-7-cyanodesacetoxycephalosporanic acid,
3-methyl-5-p-nitrophenyl-4-isoxazolylcarbonylamino-7-cyanodesacetoxycephalosporanic acid,
3-methyl-5-p-methoxyphenyl-4-isoxazolylcarbonylamino-7-cyanodesacetoxycephalosporanic acid,
3-methyl-5-p-ethoxyphenyl-4-isoxazolylcarbonyl-7-cyanodesacetoxycephalosporanic acid,
3-methyl-5-(2,6-dimethoxyphenyl)-4-isoxazolylcarbonylamino-7-cyanodesacetoxycephalosporanic acid,
3-methyl-5-p-methylsulfonylphenyl-4-isoxazolylcarbonylamino-7-cyanodesacetoxycephalosporanic acid
3-methyl-5-p-fluorophenyl-4-isoxazolylcarbonylamino-7-cyanodesacetoxycephalosporanic acid,
3-methyl-5-p-cyanophenyl-4-isoxazolylcarbonylamino-7-cyanodesacetoxycephalosporanic acid,
3-methyl-5-p-methylmercaptophenyl-4-isoxazolylcarbonylamino-7-cyanodesacetoxycephalosporanic acid,
3-methyl-5-p-dimethylaminophenyl-4-isoxazolylcarbonylamino-7-cyanodesacetoxycephalosporanic acid,
3-methyl-5-α-naphthyl-4-isoxazolylcarbonylamino-7-cyanodesacetoxycephalosporanic acid,
3-methyl-5-β-naphthyl-4-isoxazolylcarbonylamino-7-cyanodesacetoxycephalosporanic acid,
3-ethyl-5-phenyl-4-isoxazolylcarbonylamino-7-cyanodesacetoxycephalosporanic acid,
3-ethyl-5-phenyl-4-isoxazolylcarbonylamino-7-cyanodesacetoxycephalosporanic acid,
3-ethyl-5-p-chlorophenyl-4-isoxazolylcarbonylamino-7-cyanodesacetoxycephalosporanic acid,
3-isopropyl-5-phenyl-4-isoxazolylcarbonylamino-7-cyanodesacetoxycephalosporanic acid,
3-tert. butyl-5-methyl-4-isoxazolylcarbonylamino-7-cyanodesacetoxycephalosporanic acid,
3-methyl-5-p-trifluoromethylphenyl-4-isoxazolylcarbonylamino-7-cyanodesacetoxycephalosporanic acid,
3-methyl-5-cyclohexyl-4-isoxazolylcarbonylamino-7-cyanodesacetoxycephalosporanic acid,
3-cyclohexyl-5-methyl-4-isoxazolylcarbonylamino-7-cyanodesacetoxycephalosporanic acid,
3-α-furyl-5-methyl-4-isoxazolylcarbonylamino-7-cyanodesacetoxycephalosporanic acid,
3-α-thienyl-5-methyl-4-isoxazolylcarbonylamino-7-cyanodesacetoxycephalosporanic acid, respectively.

EXAMPLES 247–261

By following the procedures of Example 22 and substituting an equivalent amount of the corresponding acid chloride:

3,5-diphenyl-4-isoxazole-4-carbonyl chloride,
3-methyl-5-phenyl-4-isoxazole-4-carbonyl chloride,
3,5-dimethyl-4-isoxazole-4-carbonyl chloride,
5-benzyl-3-methyl-4-isoxazole-4-carbonyl chloride,
3-methyl-5-styryl-4-isoxazole-4-carbonyl chloride,
5-tert. butyl-3-phenyl-4-isoxazole-4-carbonyl chloride,
5-(2-furyl)-3-methyl-4-isoxazole-4-carbonyl chloride,
3-methyl-5-(3',5'-dimethyl-4'-isoxazolyl)-4-isoxazole-4-carbonyl chloride,
3-methyl-5-(2-thienyl)-4-isoxazole-4-carbonyl chloride,
3-(p-chlorophenyl)-5-methyl-4-isoxazole-4-carbonyl chloride,
3-methyl-5-methylmercapto-4-isoxazole-4-carbonyl chloride,
5-(p-chlorophenyl)-3-methyl-4-isoxazole-4-carbonyl chloride,
3-methyl-5-(o-nitrophenyl)-4-isoxazole-4-carbonyl chloride,
5-isopropyl-3-methyl-4-isoxazole-4-carbonyl chloride, and
5-methyl-3-(p-chlorophenyl)-4-isoxazole-4-carbonyl chloride,
the products obtained are
3,5-diphenyl-4-isoxazolylcarbonylamino-7-cyanodesacetoxycephalosporanic acid,
3-methyl-5-phenyl-4-isoxazolylcarbonylamino-7-cyanodesacetoxycephalosporanic acid,
3,5-dimethyl-4-isoxazolylcarbonylamino-7-cyanodesacetoxycephalosporanic acid,
5-benzyl-3-methyl-4-isoxazolylcarbonylamino-7-cyanodesacetoxycephalosporanic acid,
3-methyl-5-styryl-4-isoxazolylcarbonylamino-7-cyanodesacetoxycephalosporanic acid,
5-tert. butyl-3-phenyl-4-isoxazolylcarbonylamino-7-cyanodesacetoxycephalosporanic acid,
5-(2-furyl)-3-methyl-4-isoxazolylcarbonylamino-7-cyanodesacetoxycephalosporanic acid,
3-methyl-5-(3'-5'-dimethyl-4'-isoxazolyl)-4-isoxazolylcarbonylamido-7-cyanodesacetoxycephalosporanic acid,
3-methyl-5-(2-thienyl)-4-isoxazolylcarbonylamido-7-cyanodesacetoxycephalosporanic acid,
3-(p-chlorophenyl)-5-methyl-4-isoxazolylcarbonylamido-7-cyanodesacetoxycephalosporanic acid,
3-methyl-5-methylmercapto-4-isoxazolylcarbonylamido-7-cyanodesacetoxycephalosporanic acid,
5-(p-chlorophenyl)-3-methyl-4-isoxazolylcarbonylamido-7-cyanodesacetoxycephalosporanic acid,
3-methyl-5-(o-nitrophenyl)-4-isoxazolylcarbonylamido-7-cyanodesacetoxycephalosporanic acid,
5-isopropyl-3-methyl-4-isoxazolylcarbonylamido-7-cyanodesacetoxycephalosporanic acid, and
5-methyl-3-(p-chlorophenyl)-4-isoxazolylcarbonylamido-7-cyanodesacetoxycephalosporanic acid, respectively.

EXAMPLES 262-275

By following the procedures of Example 22 and substituting an equivalent amount of the corresponding acid chloride:

α'3-thienyl)glycyl chloride,
α-(5-ethyl-2-thienyl)glycyl chloride,
α-(5-methyl-2-thienyl)glycyl chloride,
α-(5-t-butyl-2-thienyl)glycyl chloride,
α-(2,5-dimethyl-3-thienyl)glycyl chloride,
α-(5-chloro-2-thienyl)glycyl chloride,
α-(5-bromo-2-thienyl)glycyl chloride,
α-(5-phenyl-3-chloro-2-thienyl)glycyl chloride,
α-(3,5-dimethyl-2-thienyl)glycyl chloride,
α-(5-cyclohexyl-2-thienyl)glycyl chloride,
α-(5-diethylamino-2-thienyl)glycyl chloride,
α-(4-methylsulfonyl-2-thienyl)glycyl chloride,
α-(3-ethylthio-2-thienyl)glycyl chloride, and
α-(4-cycloheptyloxy-2-thienyl)glycyl chloride, respectively, the products obtained are
7-[α-amino-(3-thienyl)acetamido]-7-cyanodesacetoxycephalosporanic acid,
D,L-7-[α-amino(5-ethyl-2-thienyl)acetamido]-7-cyanodesacetoxycephalosporanic acid,
7-[α-amino-(5-methyl-2-thienyl)acetamido]-7-cyanodesacetoxycephalosporanic acid,
7-[α-amino-(5-t-butyl-2-thienyl)acetamido]-7-cyanodesacetoxycephalosporanic acid,
7-[α-amino-(2,5-dimethyl-3-thienyl)acetamido]-7-cyanodesacetoxycephalosporanic acid,
7-[α-amino-(5-chloro-2-thienyl)acetamido]-7-cyanodesacetoxycephalosporanic acid,
7-[α-amino-(5-bromo-2-thienyl)acetamido]-7-cyanodesacetoxycephalosporanic acid,
7-[α-amino-(5-phenyl-3-chloro-2-thienyl)acetamido]-7-cyanodesacetoxycephalosporanic acid,
7-[α-amino-(3,5-dimethyl-2-thienyl)acetamido]-7-cyanodesacetoxycephalosporanic acid,
7-[α-amino-(5-cyclohexyl-2-thienyl)acetamido]-7-cyanodesacetoxycephalosporanic acid,
7-[α-amino-(5-diethylamino-2-thienyl)acetamido]-7-cyanodesacetoxycephalosporanic acid,
7-[α-amino-(4-methylsulfonyl-2-thienyl)acetamido]-7-cyanodesacetoxycephalosporanic acid,
7-[α-amino-(3-ethylthio-2-thienyl)acetamido]-7-cyanodesacetoxycephalosporanic acid,
7-[α-amino-(4-cycloheptyloxy-2-thienyl)acetamido]-7-cyanodesacetoxycephalosporanic acid, respectively.

EXAMPLE 276

Preparation of 7-acetyl 7-phenylacetamido desacetoxycephalosporanic acid a. Acylation of 7-benzaliminodesacetoxycephalosporanic acid, t-butyl ester A solution of 200 mg. of 7-benzaliminodesacetoxycephalosporanic acid, t-butyl ester in 30 ml. of dimethoxyethane is cooled to $-15°$ C under $N_2$ and 63 mg. of potassium t-butoxide was added. The red solution was then cooled to $-40°$ C and .07 ml. of acetyl chloride in 2 ml. dimethoxyethane added. The resulting straw colored solution was then immediately poured into ice cold phosphate buffer having a pH of 6.8 and extracted with chloroform. The organic extract is washed with water, then dried (sodium sulfate) and evaporated at reduced pressure. The product, 209 mg. shows $^{max}$ 1775, 1720, 163.5 cm$^{-1}$; nmr 1.58 (9H, t-butyl); 2.10 (3H, 3-CH$_3$); 2.35 (3H, COCH$_3$); 3.40 (2H, S-CH$_2$); 5.46 (1H, C$_6$H); 7.3 8.0 (5H, Φ-); 8.72 (1H, -CH=N). PPM (from TMO).

b. 7-Amino-7-acetyldesacetoxycephalosporanic acid, t-butyl ester

The above product is dissolved in 10 ml. of ethyl acetate and 1 eq. of p-toluenesulfonic acid and a drop of water added. The reaction is stirred at room temperature. The suspension is diluted with 10 ml. of ethyl acetate and then extracted with 0.2N HCl. The aqueous extracts were then adjusted to pH 8 and the free base extracted into ethyl acetate which was then dried (sodium sulphate) and evaporated at reduced pressure to leave the product, 80 mg., infrared $_{film}{}^{max}$ 3380, 3320, 1765, 1720 cm$^{-1}$.

c. 7-Phenylacetamido-7-acetyldesacetoxycephalosporanic acid, t-butyl ester i. By following the procedure of Example 21, but substituting 3.25 eq. of 7-amino-7-acetyldesacetoxycephalosporanic acid, t-butyl ester the desired product is obtained.

ii. A solution of 1 meq. of 7-benzalimino-7-acetyldesacetoxycephalosporanic acid, t-butyl ester in 15 ml. ethyl acetate is treated with 1 meq. each of phenylacetyl chloride and triethylamine at 0° C. After stirring for 15'', 1 ml. of water is added and the cooling bath removed. Stirring is continued for 1 hour. The organic layer is then washed with cold 1% aqueous NaHCO$_3$, water and 0.1N HCl, and then dried (MgSO$_4$) and evaporated at reduced pressure to deposit the product.

d. 7-Acetyl-7-phenylacetamidodesacetoxycephalosporanic acid

A solution of 100 mg. of the previous examples' product in 3 ml. trifluoroacetic acid is prepared and kept at 0° C for 5''; the solvent is then evaporated at reduced pressure to leave the product.

EXAMPLES 277–298

By following the procedure of Example 276 but using the reactants below in place of acetyl chloride.

benzoyl chloride,
p-nitrobenzoyl chloride,
m-bromobenzoyl chloride,
ethyl chloroformate,
ethyl bromoacetate,
o-nitrophenylsulfenyl chloride,
phenylsulfenyl chloride,
p-toluenesulfonyl chloride,
methylsulfonyl chloride,
methyl sulfenyl cloride,
chloroacetyl chloride,
acetic anhydride,
dimethylaminomethyl chloride,
phenylacetyl chloride,
benzoylmethyl chloride,
m-piperidylcarbonyl chloride,
trifluoroacetic anhydride,
p-nitrophenyl benzoate,
5-nitrofuroyl chloride,
5-nitrothiophenecarbonyl chloride,
dimethylaminocarbonyl chloride,
perchloryl fluoride, the corresponding products are obtained:

7-benzoyl-7-(phenylacetamido)desacetoxycephalosporanic acid, and the
7-(p-nitrobenzoyl),
7-(m-bromobenzoyl),
7ethoxycarbonyl),
7-(carbethoxymethyl),
7-(o-nitrophenylsulfenyl),
7-phenylsulfenyl,
7-p-toluenesulfonyl,
7-methylsulfonyl,
7-methyl thio,
7-chloroacetyl,
7-acetyl,
7-(dimethylaminomethyl),
7-phenylacetyl,
7-benzoylmethyl,
7-(m-piperidylcarbonyl),
7-trifluoroacetyl,
7-(p-nitrophenylcarbonyl),
7-(5-nitrofurylcarbonyl),
7-(5-nitrothiophenecarbonyl),
7-(dimethylaminocarbonyl),
7-fluoro - derivatives thereof are obtained.

EXAMPLE 299

A solution of 200 mg of 7-benzaliminodesacetoxycephalosporanic acid, t-butyl ester in 30 ml of dimethoxyethane is cooled to −35° C under a nitrogen atmosphere; 63 mg of potassium t-butoxide is added. A stream of perchloryl fluoride diluted with nitrogen gas is then passed through the solution until the red color becomes a pale yellow. The excess fluorinating agent is purged from the reaction by the nitrogen stream. The solution is diluted with chloroform and the result quickly filtered through a silica gel column. The solution is evaporated at reduced pressure to provide 7-fluoro-7-benzaliminodesacetoxycephalosporanic acid, t-butyl ester. The product is taken up in chloroform, 5 ml, and 100 mg phenol added at room temperature. The reaction is monitored by nmr observation of the C-6 proton. When complete, the solvents are evaporated at reduced pressure at room temperature or below. The residue, containing 7-benzalimino-7-phenoxydesacetoxycephalosporanic acid, t-butyl ester is taken up in 25 ml. of cloroform at 20° C. Phenoxyacetyl chloride, 80 mg., is added. After 20 minutes, 0.5 ml. of water is added as well as 60 mg. of triethylamine. The reaction is stirred at 20 ± 5° C for 3 hours, then washed with 3 × 20 ml. of 5% aqueous sodium bicarbonate solution, water and 1 × 20 ml. of cold 1N HCl. The organic solution is dried (Na$_2$SO$_4$) and evaporated to deposit the product, 7-phenoxyacetamido-7-phenoxydesacetoxycephalosporanic acid, t-butyl ester. The free acid is prepared by dissolving this residue in 1 ml. of trifluoroacetic acid (at 0° C) then warming to room temperature over a 5 minute span, followed by evaporation of the trifluoroacetic acid.

EXAMPLES 300–311

By following the preceding example but substituting for phenol:

1 eq. isopropyl alcohol,
1 eq. benzyl alcohol,
1 eq. p-nitro phenol,
1 eq. dimethylamine,
1 eq. diethylamine,
1 eq. n-methylbenzylamine,
1 eq. thiophenol,
methanol,
ethanol,
methanethiol,
acetic acid, benzoic acid, the followng products are obtained:
7-phenoxyacetamido-7-isopropoxy-desacetoxycephalosporanic acid, and the
benzyloxy -
p-nitrophenoxy-
dimethylamino -
diethylamino -
n-methylbenzylamino -
phenylthio -
methoxy -
ethoxy -
methylthio -
acetoxy -
benzoyloxy - derivatives thereof are obtained.

EXAMPLE 312

7-Aminocephalosporanic acid, t-butyl ester.

To 50 ml. peroxide free dioxane was added dropwise, at 5° to 10° C, 5 ml. concentrated sulphuric acid in a pressure bottle. Then 5 g. 7-aminocephalosporanic acid and 25 ml. liquid iso-butylene were added. The bottle was sealed and shaken at room temperature for two (2) hours. The reaction mixture was then cooled to −70° C and poured into an ice-cold mixture of 20 gr. sodium bicarbonate in 250 ml. water and 125 ml. ethyl acetate. The aqueous layer was then washed several times with ethyl acetate. The organic extracts were washed with water, dried over magnesium sulphate, and evaporated to dryness. The residue solidified and was triturated with cyclohexane. The solid was filtered off to give 3.5 grams of the desired product. MP- 105°–107° C.

EXAMPLE 313

N-Benzylidene-7-aminocephalosporanic acid, t-butyl ester.

15.5 milli-equivalents 7-aminocephalosporanic acid, t-butyl ester were dissolved in 100 ml. benzene. this was followed by the addition of 15.5 milli-equivalents benzaldehyde and 10 grams magnesium sulphate. The reaction was allowed to proceed at room temperature overnight. The magnesium sulphate was removed by filtration and the filtrate was evaporated to dryness in vacuo to leave the desired product as a yellow oil in 82% yield.

EXAMPLE 314

N-Benzylidene-7-acetyl-7-aminocephalosporanic acid, t-butyl ester.

3.2 milliequivalents N-Benzylidene-7-amino-cephalosporanic acid, t-butyl ester were dissolved in 25 ml anhydrous DME and cooled to −40° C. Then 3.2 millie- quivalents potassium t-butoxide were added followed by the addition after 5 minutes of 3.5 equivalents acetyl chloride. The reaction was completed in about 5 minutes. The reaction mixture was poured into water, washed with chloroform, dried over magnesium sulphate, and evaporated to dryness in vacuo to give the desired product as a solid. Yield - 75%.

EXAMPLE 315

7-Acetyl-7-aminocephalosporanic acid, t-butyl ester 5.5 equivalents.

N-Benzylidene-7-acetyl-7-aminocephalosporanic acid, t-butyl ester was dissolved in 500 ml. ethyl acetate and 11 equivalents p-toluenesulphonic acid and 11 equivalents water were added. The reaction mixture was shirred at room temperature for four (4) hours. A solid precipitated out. This solid was removed by filtration and distributed between chloroform and dilute sodium bicarbonate in a separatory funnel. The chloroform layer was washed with water, dried over magnesium sulphate and evaporated to dryness to give the desired free amine as a solid in 55% yield.

EXAMPLE 316

7-Acetyl-7-phenylacetamido-cephalosporanic acid. 5.3 milliequivalents 7-acetyl-7-phenylacetamidocephalosporanic acid, t-butyl ester were treated with 2 ml. trifluoro-acetic (TFA) acid for 2 minutes. The TFA was removed by evaporation in vacuo. The residual oil was dissolved in chloroform and washed into dilute sodium bicarbonate. The bicarbonate layer was washed with chloroform, acidified to pH 1.5 with dilute hydrochloric acid and extracted with methylene chloride. The latter extracts were washed over magnesium sulphate and evaporated to dryness to give the desired acid as a solid in 27% yield.

What is claimed is:

1. A compound of the formula:

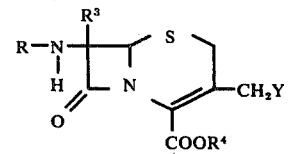

wherein $R^3$ is selected from the group consisting of phenylthio and substituted phenylthio wherein said substituent is selected from the group consisting of halogen, hydroxy, amino, nitro and lower alkyl; $R^4$ is selected from the group consisting of hydrogen, lower alkyl, trichloroethyl, benzyl, methoxybenzyl, and benzhydryl; Y is selected from the group consisting of hydrogen, acetoxy, pyridinium, and hydroxy; and R is selected from the group consisting of

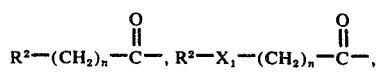

and

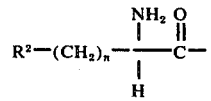

wherein $n$ is zero or one, $X_1$ is O or S, and $R^2$ is selected from the group consisting of thienyl, phenyl, and mono and disubstituted phenyl and thienyl wherein said substituents are selected from the group consisting of chloro, bromo, nitro, lower alkyl, and lower alkoxy; and pharmaceutically acceptable salts thereof.

2. The compound of claim 1 wherein $R^3$ is phenylthio or nitrophenylthio; Y is hydrogen or acetoxy; and R is

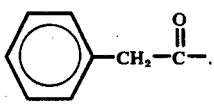

3. The compound of claim 2 wherein $R^3$ is nitrophenylthio; Y and $R^4$ are both hydrogen.
4. The compound of claim 2 wherein $R^3$ is nitrophenylthio; Y is acetoxy; and $R^4$ is hydrogen.
5. The compound of claim 2 wherein $R^3$ is phenylthio; Y and $R^4$ are both hydrogen.
6. The compound of claim 2 wherein $R^3$ is phenylthio; Y is acetoxy; and $R^4$ is hydrogen.
7. The compound of claim 1 wherein $R^3$ is phenylthio; Y is acetoxy or hydrogen; and R is

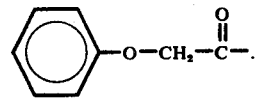

8. The compound of claim 7 wherein Y and $R^4$ are both hydrogen.
9. The compound of claim 7 wherein Y is acetoxy and $R^4$ is hydrogen.

* * * * *

UNITED STATES PATENT AND TRADEMARK OFFICE
CERTIFICATE OF CORRECTION

PATENT NO. : 4,026,886

DATED : May 31, 1977

INVENTOR(S) : Joseph Edward Dolfini et al

It is certified that error appears in the above-identified patent and that said Letters Patent are hereby corrected as shown below:

Abstract page, in the title, "Arylthiocephalosporins" should read --Arylthio Cephalosporins--.
Column 1, line 1 in the title, "Arylthiocephalosporins" should read --Arylthio Cephalosporins--.
Column 2, line 7, "chlorobromo" should read --chloro- bromo- --.
Column 14, line 23 "methoxybenzyl" should read --methoxybenzoyl-
Column 14, line 38, insert a hyphen after "4".
Column 14, line 47, insert a hyphen after "6".
Column 17, line 19, "product" should read --products--.
Column 23, line 68, after "7" insert -- -( --.
Column 26, line 60, the formula should read

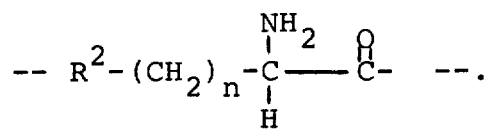

Signed and Sealed this

Sixth Day of September 1977

[SEAL]

Attest:

RUTH C. MASON
*Attesting Officer*

LUTRELLE F. PARKER
*Acting Commissioner of Patents and Trademarks*